United States Patent [19]
Grat

[11] 4,050,822
[45] Sept. 27, 1977

[54] DROP MEASURING APPARATUS, AND A METHOD OF EVALUATING MATERIALS WETTABILITY

[75] Inventor: Felix R. Grat, Lake Hiawatha, N.J.

[73] Assignee: Rame-Hart, Inc., Mountain Lakes, N.J.

[21] Appl. No.: 665,792

[22] Filed: Mar. 10, 1976

[51] Int. Cl.² ............................................ G01N 13/02
[52] U.S. Cl. .................................... 356/171; 73/64.4; 350/85
[58] Field of Search ...................... 73/64.4, 104; 356/3, 356/21, 140, 171; 350/10, 85, 86

[56] References Cited
U.S. PATENT DOCUMENTS

| | | | |
|---|---|---|---|
| 3,525,255 | 8/1970 | Orr | 73/64.4 |
| 3,535,043 | 10/1970 | Hong | 356/171 |
| 3,618,374 | 11/1971 | Miller | 73/64.4 |

Primary Examiner—John K. Corbin
Assistant Examiner—R. A. Rosenberger
Attorney, Agent, or Firm—Thomas N. Neiman

[57] ABSTRACT

The apparatus comprises means usable in the novel method for evaluating materials wettability, as well as measuring the contact angle of a liquid drop, the same comprising a structure for measuring the height of a drop deposited on a material, in that the height of the drop is indicative of both the contact angle of the drop and the wettability of the material upon which the drop is deposited. Thus, the apparatus comprises a platform on which to receive a drop (directly, or via an interposed substrate or like subject "material") — of predetermined composition and volume — and means coupled to the platform for gauging the height of the drop, from its chord interfaced with the platform (or substrate or "material"), to its topmost surface. The novel methods comprehend the measuring of drops on materials, the wettability of which materials needs to be determined, and comparing the derived measurements against "standard" drop measurements of same materials which have acceptable and unacceptable wettability, or comparing the derived measurements against heights of same drops of same volume, the contact angles of which latter drops are known, to ascertain the contact angles of the drops under examination.

17 Claims, 8 Drawing Figures

DROP MEASURING APPARATUS, AND A METHOD OF EVALUATING MATERIALS WETTABILITY

This invention pertains to measuring apparatuses and methods, such as contact angle goniometers and contact angle measuring methods, but particularly it pertains to quite dissimilar liquid-drop measuring apparatus and methods; especially it is concerned with measurement of drop heights and, therefrom, indirect or interpolated drop contact angle measurements.

In laboratories, and in industry, there has been a long-felt need for a simple apparatus and method for determining the wettability of materials — however this might be defined: as wettability, or spreadability, or repellancy — as a tool toward evaluating the cleanliness of surfaces, the acceptability of coatings, and like treatments of surfaces or whatever, the natures of which, commonly, cannot be detected and evaluated by the human eye alone. Now, to date, contact angle goniometers have been employed to meet the requirement, as the contact angle of a liquid-drop deposition on the surface of a test material is a good gauge of the wettability of the material. Contact angle goniometers, however, are precision devices which, in turn, causes them to be rather expensive. Also, being of high precision, they can offer most accurate and finely divided readings. Often enough in the laboratory, and usually in industry, such accuracy is more than is required.

In industry, for instance where micro-electronics are deposited upon ceramics, crystalline substances, and the like, it is essential to ascertain that the microelectronics-receiving substrate is clean — and it is essential to be able to determine this rapidly. Now, a contact angle goniometer can readily evaluate the cleanliness of such substrates, but with uncommon precision, not uncommon rapidity.

What industry sorely needs, and laboratories to a large measure, is an apparatus usuable as a materials-wettability evaluating device, which will rapidly, and with ample accuracy, provide either, as desired, a reading of the contact angle of the drop, or a "go"/"no-go" reading—an apparatus which, to this end, will measure the petinent parameter of a drop deposited on a material the wettability of which must be determined. As a corollary thereto, there is a need as well for a simple and expedient method of evaluating materials wettability or drop contact angles.

It is an object of this invention to set forth just such a simple and expedient method, as well as the above-noted, facile apparatus.

Particularly, it is an object of this invention to define and disclose a liquid-drop measuring apparatus, for use as a materials-wettability evaluating device, comprising first means for accepting a liquid-drop deposition and supporting such a liquid drop thereon; and second means coupled to said first means for measuring the height of a liquid drop which has been deposited and is supported on said first means.

It is also an object of this invention to set forth a method of measuring the contact angle of a liquid drop, comprising the steps of: first, ascertaining the height of a liquid drop of given volume deposited on a material; and second, comparing the ascertained height against heights of same liquid drops of the same volume, the contact angles of which are known.

It is yet another object of this invention to dislcose a method of evaluating materials wettability, comprising the steps of: first, ascertaining the height of a liquid drop of given volume deposited on a material the wettability of which is to be determined; and second, comparing the ascertained height against heights of same liquid drops of the same volume attained on such material the wettability of which latter material is known to be acceptable and unacceptable.

Further objects of this invention, as well as the novel features thereof, will become more apparent by reference to the following description, taken in conjunction with the accompanying figures, in which.

Figure 6:
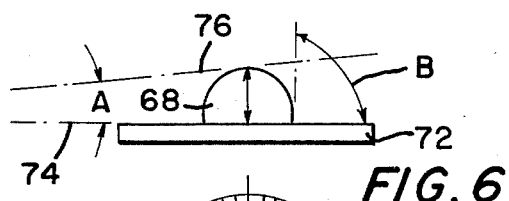
Figure 6A:
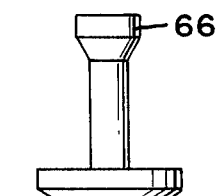
Figure 6A:
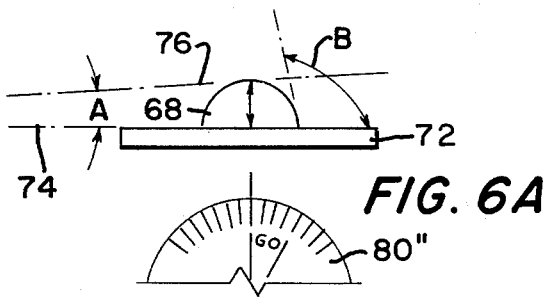
Figure 6B:
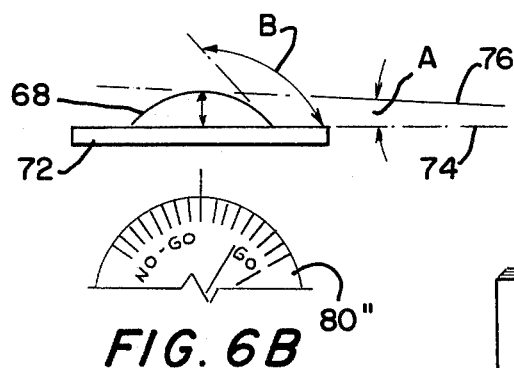
Figure 5:
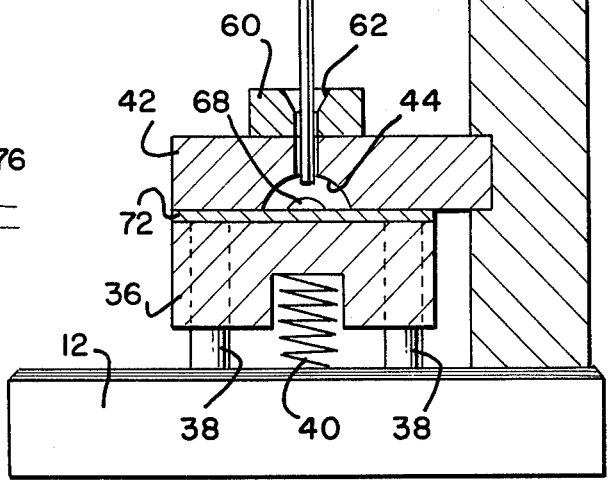
FIG. 5 is a cross-sectional view taken along section 5—5 of FIG. 2.

FIGS. 6, 6A, and 6B are diagrammatic/pictorial illustrations of drops which present, respectively, an ideal height and contact angle, an acceptable height and contact angle, and an unacceptable height and contact angle.

As shown in the figures, a liquid-drop measuring apparatus 10, according to an embodiment thereof, comprises a base 12 to which is mounted a microscope support 14. The latter supports a microscope 16 by means of a pivot arrangement 18. Arrangement 18 comprises a tapered trunnion pin 20 which is integral with, and extends laterally from the microscope 16, and which is received by a complementary tapered bearing 22. Bearing 22 is enclosed by a bearing support 24 which has a bore 26 formed therein. Bore 26 is straight, and receives the straight, outer surface of the bearing 22. An annulus 28 is received in a recess therefor, in an outer wall of the support 24, for centralizing and securing the bearing 22 in place. Machine screws 30 fasten the annulus 28 to the support 24.

Base 12 is supported in elevation by threaded leveling pins 32 — of which there are three. Pins 32 are used to effect an accurate leveling of the base 12 and apparatus 10, by reference to a level 34 fixed in the uppermost surface of base 12.

A reference platform 36 is slidably supported on four pins 38 upon base 12, and a compression spring 40 is interposed between the underlying surface of theplatform 36 and the uppermost surface of the base, to urge the platform upwardly. A limit-stop element 42, which has an arcuate cover 44 formed therein, delimits the upward movement of the platform 36. Element 42 is carried by, and extends laterally from a stanchion or upright 46 which is mounted to the base 12. The cove 44 is presented to define a space in which a drop can be deposited on the platform 36. The limit-stop element 42, however, is provided to define a delimiting, starting reference for the setting chord of the drop to be measured.

Lamp assembly 48 is carried on a limb 50 fixed to the stanchion 46 for illuminating the uppermost surface of the platform 36 and, thus, to provide an illuminated background for the microscope 16. The lamp assembly 48 has a line cord 52 (only a portion of which is depicted) for connection thereof to a source of line current.

The stanchion 46 has a cantilevered arm 53 in which there is formed a bore 54; the latter slidably receives a micro-pipette dispenser 56. The bore includes a shoulder stop 58 which restricts the insertion of the disperser, and further has detent arrangement 59 to locate the dispenser 56 for purposes explained in the ensuing text. A centralizer 60 with a tapered, locating access 62 receives the dispensing tip 64 of the dispenser from which a precisely measured volume of liquid is evacuated by means of the plunger 66 — for deposition of a drop 68 upon material supported on the platform 36.

The microscope 16 has a right-angularly disposed eyepiece 70 through which one may sight — to view the platform and the drop 68. In the illustrations, a material 72, which is to be evaluated for its wettability, has the drop 68 formed thereon. The viewing aspect line 74 signifies the visual observation of the base or chord of the drop 68 upon the material 72; the viewing aspect line 76 is representative of the visual observation to be made of the uppermost surface of the drop 68.

Figure 3:
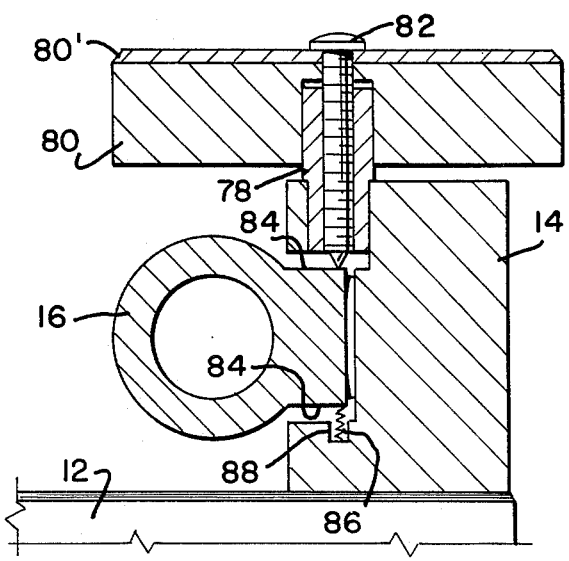
FIG. 3 is a cross-sectional view taken along section 3—3 of FIG. 1.

The cooperating structure which enables the visual alignment of the microscope 16 with the chord of the drop 68, and its scanning elevation to the topmost surface of the drop, is best seen in FIG. 3. The microscope support 14 has an axle or shaft 78 fixed thereto and extending therefrom. A graduation-marked dial and wheel 80 is rotatably carried on the shaft 78. A threaded pin 82 is threadedly engaged with both the dial and wheel 80 and the shaft 78, and a pointed, terminal end of the pin projects from shaft 78 (opposite the dial and wheel 80). A flatted side of the body of the microscope 16 presents a bearing surface 84 with which the pin end engages. Another bearing surface 84' (opposite the other) receives the bias of a compression spring 86 which is nested in a recess 88. Spring 86 urges the viewing end of microscope 16 upwardly (to depress the objective end) and, conversely, the threaded pin 82 is provided to depress the viewing end of the microscope. As already noted, pin 82 is threadedly engaged with the dial and wheel 80, thus, as the dial and wheel 80 is rotated, it causes the pin to move axially through the shaft 78. Accordingly, the dial and wheel 80 and pin 82 are used to cause the microscope to slue through an arc where viewing may be made along aspect line 74 and from thence, upwardly.

In operation, the apparatus 10 is placed on a vibration-free support. Leveling pins 32 are manipulated to center a bubble in the level 34, and the lamp assembly line cord 52 is connected to an electrical source. The reference platform 36 is depressed on pins 38 against spring 40, and the "sample" material 72 is placed on platform 36 —below tip 64 of the dispenser 56. Then the platform 36 is released; material 72 rises, to bear against element 42 and, thus, is optimumly located. (If the microscope 16 requires focusing, to define a sharp crosshair, this would be done at this time.) The dispenser 56 is withdrawn from the arm 53 and charged with liquid, and then returned to the apparatus. The dispenser 56 is inserted in bore 54 and centralizer 60 until it seats against the shoulder stop 58. Now, the plunger 66 is depressed; while the plunger 66 is still depressed, the dispenser is raised until the detent arrangement 59 seizes it. At this time, the plunger 66 is released. While slowly rotating the wheel 80 and viewing the crosshair in the microscope 16, stop wheel rotation when the crosshair is exactly aligned with the topmost portion of the drop 68 (on material 72). The indicated reading on the dial 80' is a direct reading of the contact angle of the observed drop.

The reading in the contact angle is a derivation of the drop height; this is achieved in the design of the apparatus through the cooperation of certain critical parameters: the fineness of the thread of pin 82, the linear distance between the pin 82 and the pivot of the microscope 16, and the linear distance between the pivot and the point of deposition of the drop 68.

Figure 1:
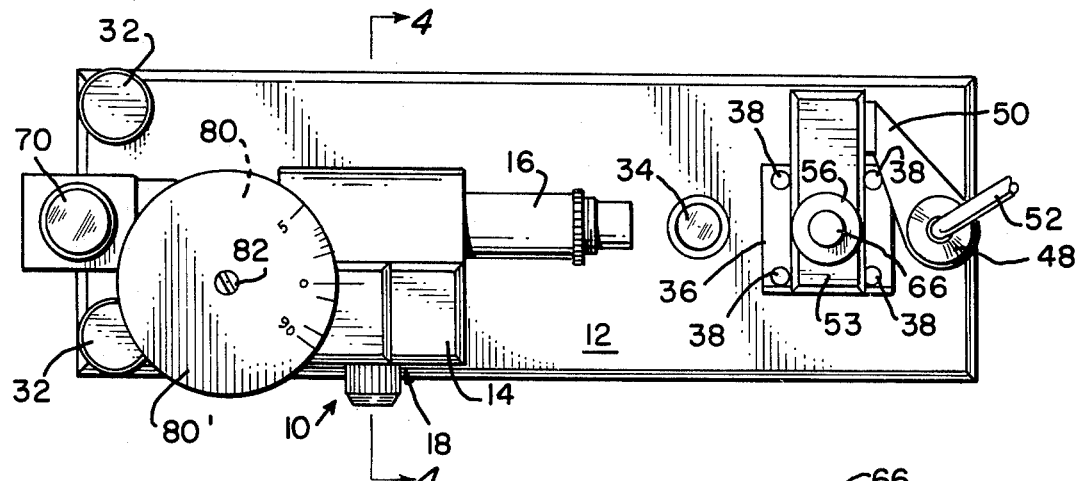
FIG. 1 is a top or plan view of the novel apparatus, according to an embodiment thereof.
Figure 2:
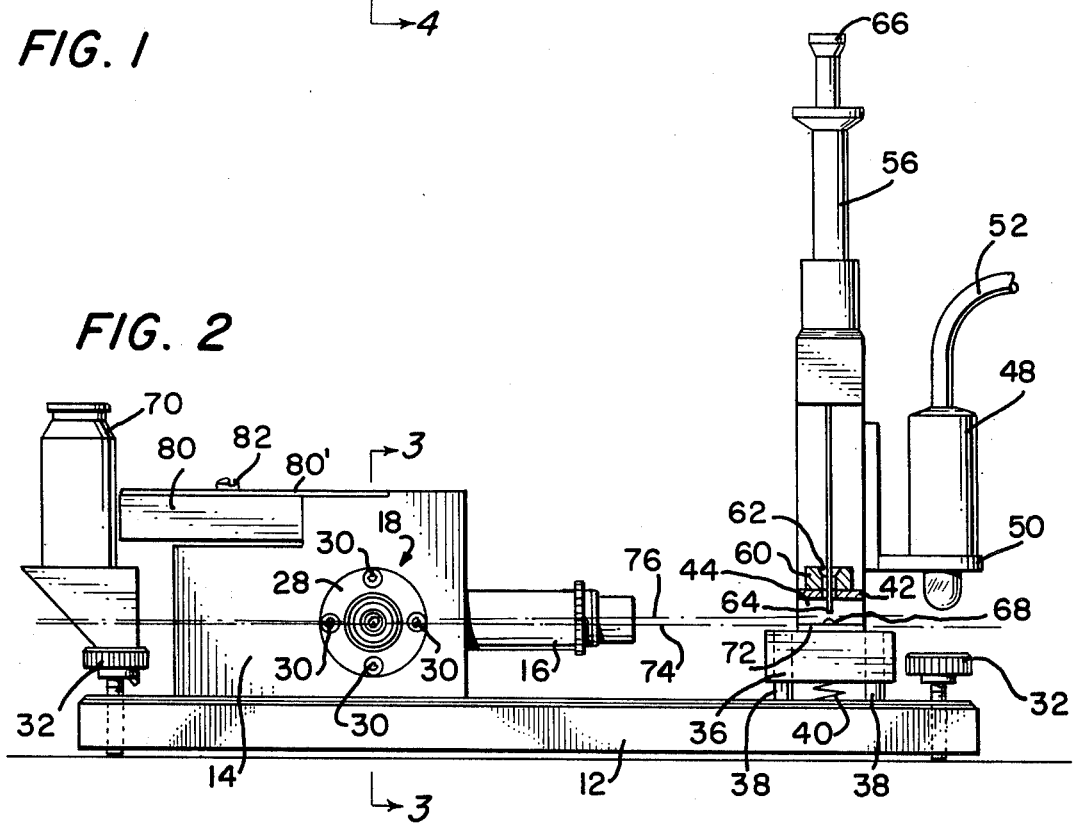
FIG. 2 is a side elevational view of the embodiment of FIG. 1, the illustration being partly in cross-section.
Figure 4:
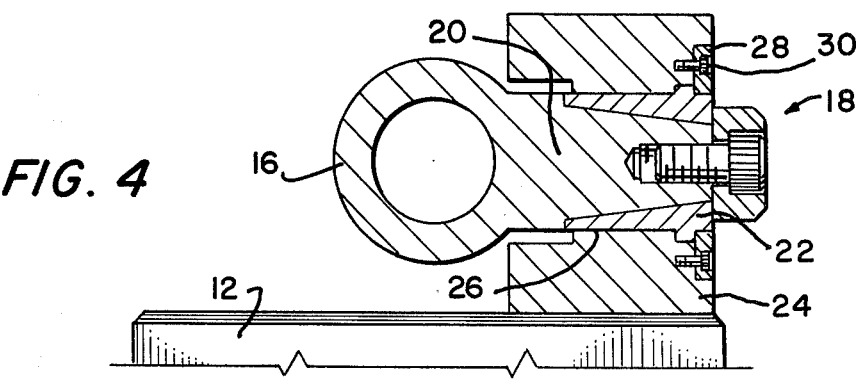
FIG. 4 is a cross-sectional view taken along section 4—4 of FIG. 1.

In FIG. 6 is shown a drop 68 on material 72 which is ideal; here the drop has a height noted by a viewing angle "A" which denotes the ideal contact angle "B" for the material under test. In FIG. 6A the viewing angle "A" is somewhat shallower than ideal and, thus, the contact angle "B" is slightly obtuse. In FIG. 6B the viewing angle "A" is quite shallow, and the contact angle is grossly obtuse. The apparatus embodiment shown in FIG. 1 has a dial 80' which gives a read-out in contact angles. However, for the purpose of presenting a quick acceptable or non-acceptable reading of the drop/material under investigation, the wheel 80 can carry an overlay dial 80'' which simply denotes "Go" and "No-Go" criteria thereon. Such an overlay dial 80'' is shown in FIGS. 6, 6A and 6B in association with the variously configured drops.

While I have described my invention in connection with a specific embodiment of apparatus therefor, and method of use, it is to be clearly understood that this is done only by way of example and not as a limitation to the scope of my invention as set forth in the objects thereof and in the appended claims. For instance, rather than translate the microscope 16 through an arc, other arrangements will occur to others, by taking teaching from my disclosure, in which the viewing optics will remain fixed — initially on the chord of the drop under investigation — and a platform like that of platform 36 can be moved in elevation against a scale of measurement (until the drop topmost portion is aligned with the optical crosshair and some measurement graduation). Such an alternative arrangement, and others which will come to mind, are quite within the ambit of my teaching. Too, the method of practicing my teaching comprehends establishing "standard" heights or contact angles for drops on materials under evaluation for purposes of comparison against the heights derived — either directly read in millimeters or fractions or decimals of an inch, or read in contact angles — to determine a correspondence, slight disparity, or grevious disparity. The "standard" heights or contact angles are those in which, for the material under test, a given drop of liquid of given volume will assume prescribed parameters. The same, then, becomes the reference against which other drops on further samples of the same material are gauged for acceptability or rejection.

In certain cases, it may be found that the drop configuration changes very rapidly. This will arise from the nature of the materials under test. In such circumstances, it will be more useful to establish a constant time value. That is, deposit the drop, wait a preset time period, and then take the measurement. In this, then, both the "standard" or reference drop, as well as all ensuing test drops, are to be measured after awaiting the same preset time period. With all drops, the reference as well as the test drops, subject to the same constant time value, the results will be that more valid. An optimum constant time value will have to be established, by experimentation, with different materials. Some materials, it may be found, will require no deferred-time measurements.

I claim:

1. Liquid-drop measuring apparatus, for use as a materials-wettability evaluating device, comprising:
    first means for accepting a liquid-drop deposition and supporting such a liquid drop thereon; and
    second means coupled to said first means for measuring the height of a liquid drop which has been deposited and is supported on said first means; wherein
    said first means comprises a platform having a planar surface on which to support a liquid drop, in order that said surface and the chord of a drop supported thereon will define a contacting interface therebetween:
    said second means comprises means for gauging the elevation of an uppermost surface of such a drop from said surface of said first means; and
    said gauging means comprises viewing means for visually fixing on a drop supported on said surface of said platform, and means for moving said viewing means in order visually to fix on the chord of such drop and to scan to the uppermost surface of such drop.

2. Apparatus, according to claim 1, wherein:
    said gauging means further comprises scale means having a plurality of graduation markings thereon.

3. Apparatus, according to claim 2, wherein:
    said graduation markings define contact angle measurements.

4. Apparatus, according to claim 2, wherein:
    said graduation markings define go and no-go, i.e., acceptable and non-acceptable elevation measurements.

5. Apparatus, according to claim 2, wherein:
    said graduation markings define linear elevation measurements.

6. Apparatus, according to claim 1, wherein:
    said viewing means includes alignment means for effecting visual coincidence of said alignment means with both the chord of such drop and the uppermost surface of such drop.

7. Apparatus, according to claim 6, wherein:
    said viewing means comprises a optical device, and said alignment means comprises a horizontal crosshair.

8. Apparatus, according to claim 1, wherein:
    said gauging means further comprises scale means having a plurality of graduation markings thereon; and
    said scale means is coupled to said moving means, whereby said scale means exhibits movement coincident with said moving means.

9. Apparatus, according to claim 8, further including:
    indicator means, mounted in adjacency to said scale means, for indicating movement of said scale means relative thereto, and for exhibiting displacement of said graduation markings relative to said indicator means.

10. Apparatus, according to claim 1, further including:
    means coupled to said platform for illuminating said platform.

11. Apparatus, according to claim 1, further including:
    third means defining a base for supporting said first and second means thereon; and
    means coupled to one of said first, second and third means for receiving a liquid-drop dispenser.

12. Liquid-drop measuring apparatus, for use as a materials-wettability evaluating device, comprising:
    first means for accepting a liquid-drop deposition and supporting such as liquid drop thereon; and
    second means coupled to said first means for measuring the height of a liquid drop which has been deposited and is supported on said first means; wherein
    said first means comprises a platform having a planar surface on which to support a liquid drop, in order that said surface and the chord of a drop supported thereon will define a contacting interface therebetween; and
    said second means comprises means for gauging the elevation of an uppermost surface of such a drop from said surface of said first means; further including
    a base; wherein
    said first and second means are mounted on said base;
    said platform is supported in elevation upon said base;
    said platform is movably mounted on said base, for movement toward and away from said base; and further including
    means mutually engaging both said base and said platform for urging said platform away from said base; and
    means coupled to said base for delimiting movement of said platform away from said base to a predetermined optimum position.

13. A method of evaluating materials wettability, comprising the steps of:
    first, ascertaining the height of a liquid drop of given volume deposited on a material the wettability of which is to be determined; and
    second, comparing the ascertained height against heights of same liquid drops of the same volume attained on such material the wettability of which latter material is known to be acceptable and unacceptable.

14. A method, according to claim 13, wherein the first step comprises:
    depositing a liquid drop of given volume on the material to be evaluated for wettability, so that the drop defines it chord upon the material and forms a globule with a topmost surface; and
    measuring the height or distance between the chord and topmost surface.

15. A method, according to claim 13, wherein the second step comprises:
    depositing liquid drops of a given volume on samples of material of the type to be evaluated which are known to be acceptable, marginally acceptable, and unacceptable as to the wettability thereof;
    ascertaining the heights of the drops on the samples of material;
    recording the latter ascertained heights as comparative-standard references; and
    noting a same or near likeness of the height of the drop of the material under evaluation to the heights of the recorded references.

16. A method, according to claim 15, further including the step of:
    waiting a predetermined period of time, following the deposition of the liquid drops on the samples of material, before ascertaining the heights thereof; and waiting a same predetermined period of time, following the deposition of the liquid drop on the material to be evaluated, before ascertaining the height thereof.

17. A method of measuring the contact angle of a liquid drop, comprising the steps of:

first, ascertaining the height of a liquid drop of given volume deposited on a material; and second, comparing the ascertained height against heights of same liquid drops of the same volume, the contact angles of which are known.

* * * * *